United States Patent [19]
McGill et al.

[11] 4,025,070
[45] May 24, 1977

[54] RESPIRATORY EXERCISER

[75] Inventors: Lee E. McGill, Albany; Raymond D. Von Alven, San Raphael, both of Calif.

[73] Assignee: Cutter Laboratories, Inc., Berkeley, Calif.

[22] Filed: Apr. 19, 1976

[21] Appl. No.: 678,282

[52] U.S. Cl. ................................. 272/99; 128/2.08
[51] Int. Cl.² ..................... A63B 23/00; A61B 5/08
[58] Field of Search .................... 272/99; 128/2.08; 46/44

[56] References Cited
UNITED STATES PATENTS

| | | | |
|---|---|---|---|
| 3,695,608 | 10/1972 | Hanson | 272/99 |
| 3,754,546 | 8/1973 | Cooper | 128/2.08 |
| 3,936,048 | 2/1976 | Dunlap et al. | 272/99 |

FOREIGN PATENTS OR APPLICATIONS

| | | | |
|---|---|---|---|
| 8,662 | 4/1903 | United Kingdom | 272/99 |
| 685,815 | 1/1953 | United Kingdom | 272/99 |

*Primary Examiner*—Jerome Schnall
*Attorney, Agent, or Firm*—Robert E. Allen; Bertram Bradley

[57] ABSTRACT

The device is a disposable compact unit comprising a transparent column with an aperture at its base, an air float within the column and with the column mounted on a closed container. A conduit joins the top of the column to an opening into the container. The container is also equipped with a breathing tube and a variable aperture means for varying the size of another opening into the container. By inhaling through the breathing tube, a patient can judge his capacity for alveolar expansion by the height to which the air float rises. Adjustment to any patient's capacity can be easily made by changing the opening in the variable aperture means.

11 Claims, 8 Drawing Figures

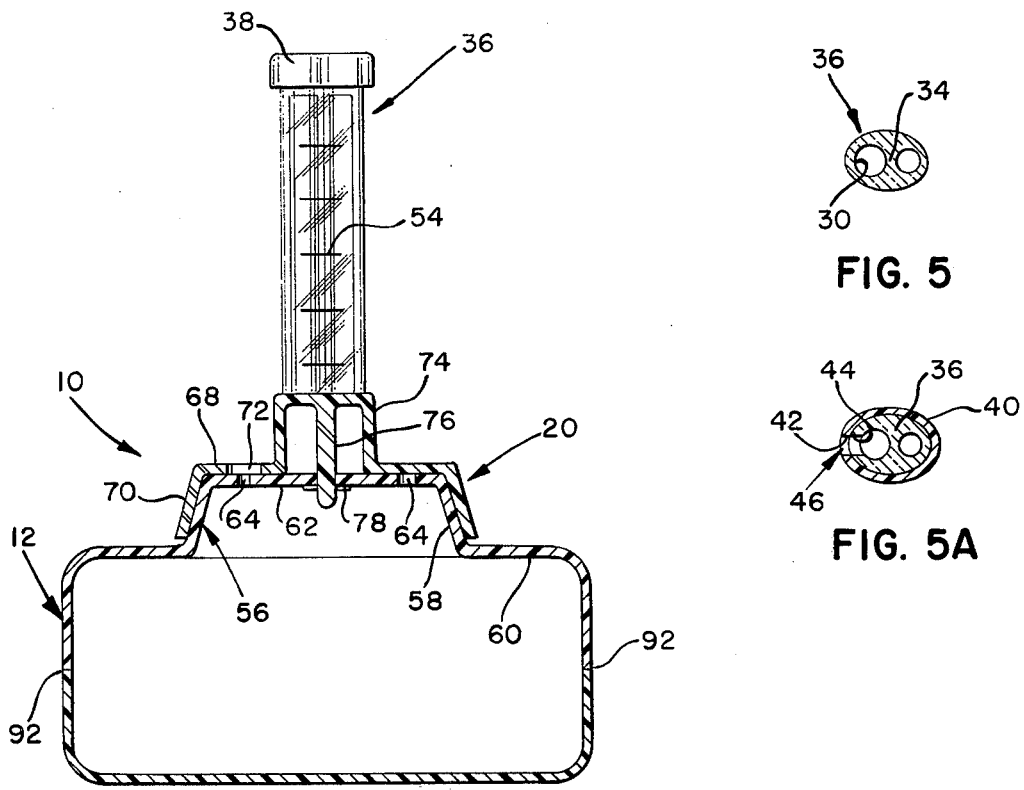
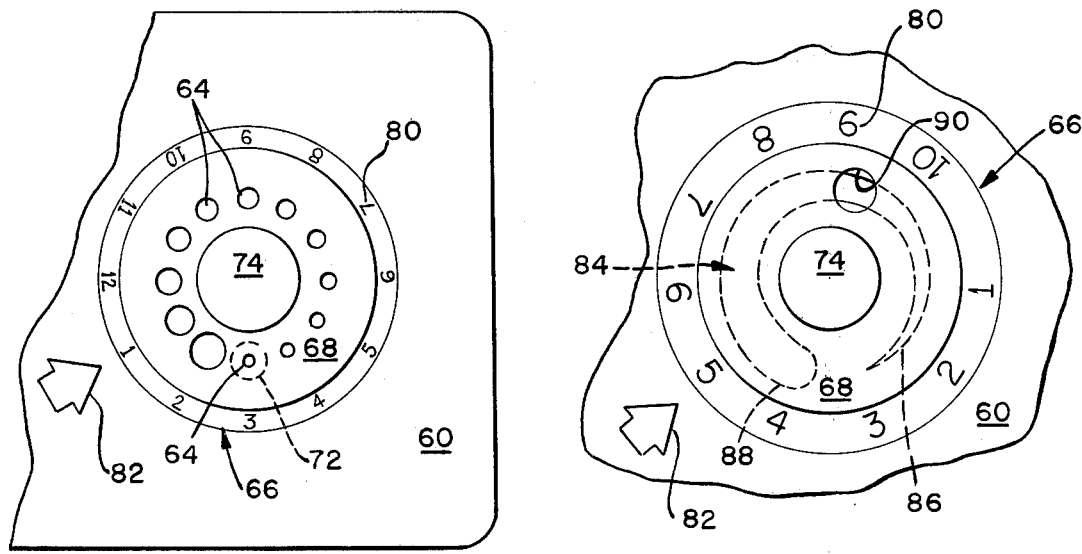

4,025,070

RESPIRATORY EXERCISER

BACKGROUND OF THE INVENTION

This invention relates to a respiration exercising device and in particular to a device for enhancing inspiration for improvement of pulmonary performance.

One of the main causes for slow recovery of postoperative patients has been inadequate oxygen exchange in the lungs resulting from shallow breathing accompanying the use of general anesthesia. This condition can lead to partial or complete collapse of the lungs and to pneumonia.

Various methods have been proposed for preventing such pulmonary complications including instructions to the patient to breathe deeply, coughing exercises, and the use of blow bottles or the like to enhance expiration. Such methods of lung exercise have not been too successful since the alveoli are not adequately expanded.

Recognizing the greater benefits from methods employing positive pressure breathing, i.e., dilating bronchi and expanding unventilated alveoli by positive inhalation, several devices have been introduced to stimulate the patient in improving his inspiratory capacity. One such device is disclosed in U.S. Pat. No. 3,754,546. A patient inhaling through a tube at the top of a cylinder causes a piston to rise until it makes contact with a preset post. As long as the patient continues to inhale, the contact causes a light to glow. By changing the setting of the post, greater or lesser inhalation capacity is required to obtain a light signal. Although the piston and cylinder portion is relatively inexpensive and disposable, the signal unit which is detachable, is not, so that extensive use of the device becomes impracticable.

Another device which is in use consists of three light weight balls each in three vertical tubes interconnected at their tops and with a vent at the bottom of each tube. When the patient inhales through a breathing tube attached to the first tube, one or more balls will rise to the top of their respective tubes, depending on the strength of the inhalation. Although the device is inexpensive and disposable, it lacks versatility since it has the capability for measuring only three values of inspiratory capacity.

Objects of the present invention are, therefore, to provide a device for improving inspiration capacity, to provide a device which is useful for any individual regardless of his lung capacity, and to provide an improved device which is inexpensive, disposable and convenient to use, requiring a minimum of instruction and supervision.

SUMMARY OF THE INVENTION

The device of the present invention comprises a closed container with three openings and a transparent vertical tube secured to the container. An air floatable member normally rests near the bottom of the transparent tube and is responsive to exterior air forced through an aperture in the tube below the floatable member to cause it to rise upwardly in the tube. One of said openings connects with a breathing tube. The second of said openings is connected to one end of a conduit whose other end joins the top of the transparent tube. The third opening has variable aperture means which has the effect of varying over a wide range the amount of air which flows through the tube aperture. Thus when an individual inhales through the breathing tube which removes air from the container, air rushes into the bottom of the tube and causes the floatable member to rise. The height to which it will rise will be governed by the amount of air entering the container which is distributed between the tube aperture and the third opening whose size is easily altered at will. The smaller the third opening, the higher the floatable member will rise at any given period in a therapeutic course of exercise. Indica on the transparent tube can be calibrated for inspiratory capacity.

One embodiment of the device includes variable aperture means for the third opening in which a cap member with one aperture slidingly engages a portion of the container, this portion having a series of progressively enlarging, circularly arranged holes. The cap aperture registers with one of the holes in the container while sealing off the remaining holes. Conversely, in another embodiment, the series of holes of varying size are in the cap member and the single hole is in the container. Still another embodiment of the variable aperture comprises a circular slot in the container increasing in width from one end to the other and with an aperture in a rotatable cap arranged to register with a portion of the slot.

The invention will be better understood and additional objects and advantages will become apparent from the following description of the preferred embodiments and as illustrated in the drawings.

BRIEF DESCRIPTION OF THE DRAWINGS

FIG. 4 is an end view in cross section of the device in FIG. 3 taken along line 4—4;

FIG. 5 and 5A are cross sectional views of the top and bottom portions of the transparent sight tube and connecting conduit of the device in FIG. 3 as taken along line 5—5 and 5A—5A, respectively FIG. 6 is a fragmentary plan view showing another embodiment of the variable aperture means of the device of this invention; and FIG. 7 is a fragmentary plan view showing still another version of the variable aperture means on the device of this invention.

DESCRIPTION OF A PREFERRED EMBODIMENT

Figure 1:
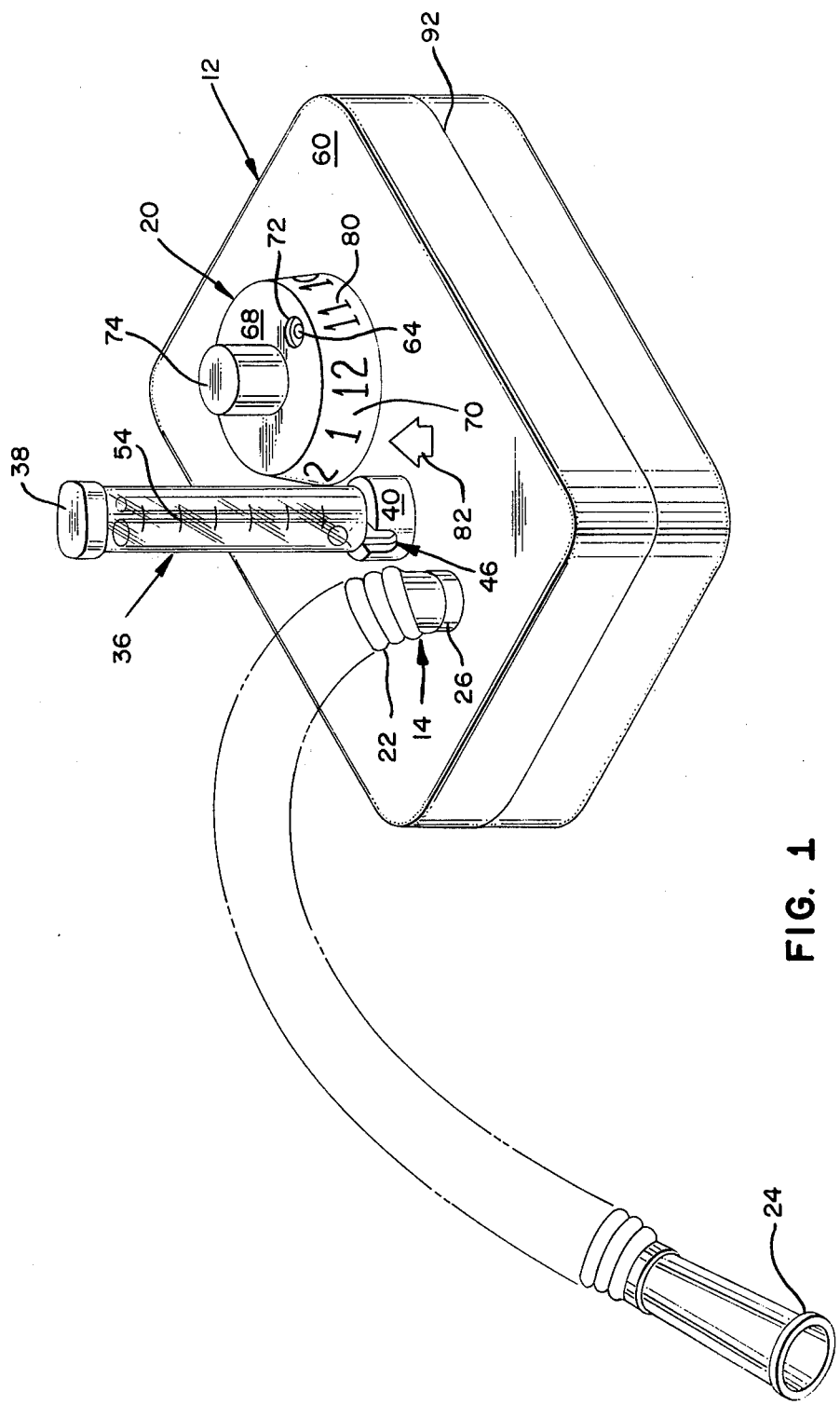
FIG. 1 is a perspective view of a preferred embodiment of the respiratory exercising device of this invention.

Referring to FIGS. 1–4, a respiratory exercising device 10 is disclosed which comprises a closed container 12 on which are mounted a breathing tube assembly 14, an air capacity indicator column 16, a conduit 18 and a variable aperture member 20. Container 12 can be any shape, e.g., circular, ovate, square, rectangular, and in this embodiment it is rectangular. Its size is not critical.

Breathing tube assembly 14 comprises a flexible tube 22 with a mouthpiece 24 and is connected to a nipple 26 which extends from container 12 and provides access to container 12.

Indicator column 16 is a vertically extending tubular element defined by a wall 28 which in this embodiment provides an inner surface 30 which is circular. The upper end of column 16 is in fluid communication with conduit 18 defined by wall 32 and in which column 16 and conduit 18 are separated by a wall portion 34. Thus walls 28, 32 and 34 comprise a unitary member 36 having column 16 and conduit 18 contained therein. The top of member 36 is sealed with cap 38. Although this preferred embodiment shows column 16 and conduit 18 as being formed by a single member 36, other means are equally functional such as a separate tube for column 16 having its top connected to a flexible tube acting as conduit 18 which extends to the container 12 apart from column 16.

Member 36 is sealingly engaged at its lower end to projection 40 on the top of container 12. Projection 40 has a cut- out portion 42 which is in alignment with a cut-out portion 44 at the lower end of column 16 to form a passageway or access 46 from column 16 to the exterior. The lower end of conduit 18 which meets the top of container 12 communicates with an opening 48 in container 12. Slightly above access 46 is a nub 50 on the inner surface 30 of column 16 which serves to support an air floatable member 52. Air float 52 is a light weight ball with a diameter somewhat less than the diameter of column 16 and made of any material which will allow it to rise upwardly when air of sufficient pressure is directed through access 46. Air float 52 can also have other shapes, e.g., cylindrical, ovate, conical, or any shape which generally conforms to the configuration of the inner periphery of column 16 be it square, ovate, circular, etc.

The walls of column 16 are of transparent material, glass or any suitable plastic, and may include indicia 54.

Figure 2:
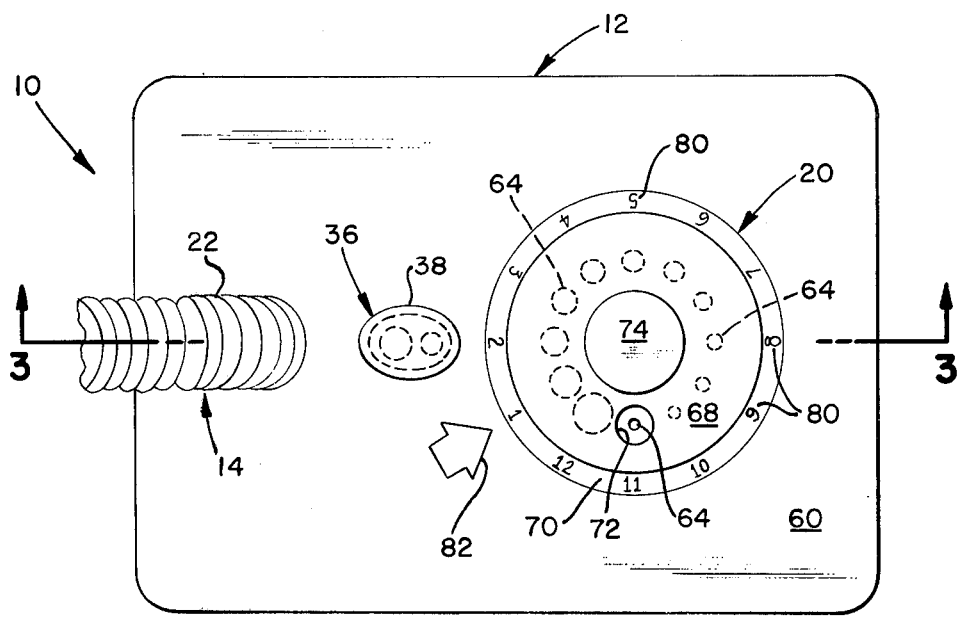
FIG. 2 is a plan view of the device of FIG. 1 showing details of the variable aperture means.
Figure 3:
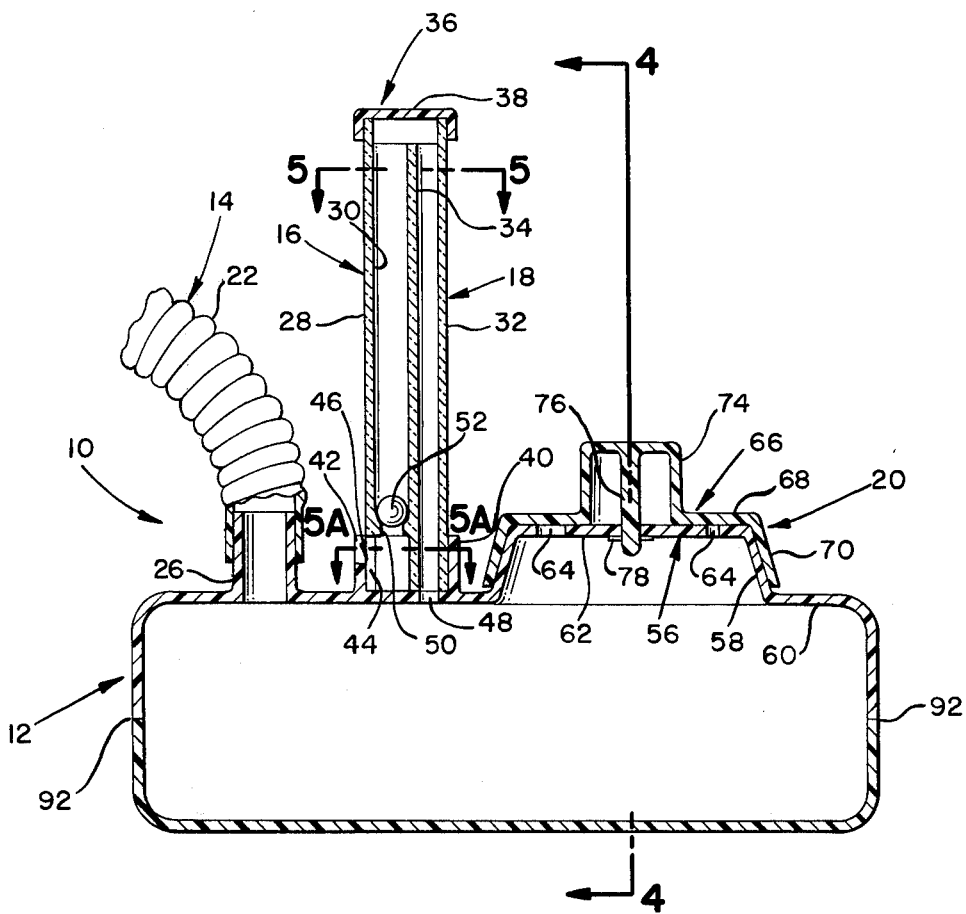
FIG. 3 is a side view in cross section of the device of FIG. 2 taken along line 3—3.

As disclosed in FIGS. 2–4, variable aperture member 20 comprises a circular base portion 56 having a side wall 58 integral with surface 60 of container 12 and a flat upper wall 62. A plurality of holes 64 having progressively increasing diameters are located in wall 62 and are arranged in a circumferential manner with the center of each hole 64 being spaced equidistantly from the center of an adjacent hole 64. A circular cap 66, having an upper wall 68 and side wall 70, sealing and sliding engages the side wall and upper wall of base portion 56. An aperture 72 is located in upper wall 68, aperture 72 having a diameter which is substantially the same as that of the largest hole 64 in base portion 56. Aperture 72 is spaced on upper wall 68 so that its center coincides with the center of any of holes 64 when cap 66 is rotated. Cap 66 has a projecting knob 74 with a center post 76 passing through wall 62 and secured by a retaining clip 78. When knob 74 is rotated, cap 66 engages and slidingly rotates on base portion 56. Numerals or other indicia 80 are located on side wall 70, spaced so as to mark off the positions of holes 64 in wall 62. A hole position indicator 82 is located on surface 60 adjacent cap 66.

Variable aperture member 20 can have other forms as long as there is a means for providing an aperture into container 12 which can be varied in size. One such modification of variable aperture member 20 is shown in FIG. 6 wherein the plurality of holes 64 are found in the upper wall 68 of cap 66 and aperture 72 is located in upper wall 62 of base portion 56. Another modification of variable aperture member 20 (FIG. 7) comprises a circular slot 84 in upper wall 62 which is narrow at one end 86 and progressively widens to the other end 88. Cap 66 has an aperture 90 whose diameter is substantially the same as the width of slot 84 at end 88.

Although the specific embodiments of the respiratory exerciser of the present invention as disclosed in FIGS. 1–7 show the opening 48 from conduit 18 leading into container 12 at a position in between the openings provided by nipple 26 and the variable aperture member 20, this arrangement is not critical in the use of the device. Other arrangements are possible and in fact these members and aperture can be positioned anywhere on the container without affecting the function of the device.

The respiratory exerciser of this invention can be made of any rigid material, preferably of a plastic which can be readily molded and sealed by heat or solvent welded. The container 12 can be formed conveniently by molding it in two parts and subsequently joining these two parts as at junction 92 after first installing cap 66.

In operation, knob 74 is rotated to line up a particular numeral 80 at indicator 82. A patient is instructed to exhale, close his mouth about the mouthpiece 24 and inhale gradually but forcibly through the mouthpiece. Air from the exterior is drawn through opening 46 in column 16 as a result of air being withdrawn from column 16 through conduit 18 and container 12 by the inspiration of air into the patient's lungs. This causes the ball 52 to rise upwardly in column 16 to a height which is related to the patient's inhalation capacity. Not all the air enters through opening 46. A portion of the air entering the container comes through the pre-set aperture in the variable aperture member 20. The smaller this pre-set aperture is, the lower the ball rises. Thus, the respiratory exerciser of this invention has the capability for providing easily and simply a means for progressively exercising the lungs. With its inherent versatility for selective control of the air, which causes the ball to float, the same device can be used by anyone regardless of the lung capacity of the individual. Furthermore, the device is inexpensive, is entirely disposable and is easily adjusted to the capacity of the individual patient.

What is claimed is:
1. A respiratory exercising device comprising:
 a. a closed hollow container,
 b. a breathing tube in communication with a first opening located at a first position on said container,
 c. variable aperture means for selectively regulating flow of air into said container and located at a second position on said container,
 d. a transparent hollow column generally vertically mounted by its base at a third position on said container and having an access opening into said column near the base of said column, said access opening being external of said container,
 e. conduit means connected at one end to the upper end of said column and in communication at its other end with a second opening in said container said first opening, said aperture means and said second aperture being in communication within the container; and
 f. an air floatable member normally positioned near the bottom of said column above said access opening and adapted for vertical movement within said column in response to flow of air through said access opening on inhaling air through said breathing tube.
2. The device of claim 1 wherein said column and said conduit means are combined to form a unitary member comprising a vertical tubular chamber with a closed top and having a partition extending longitudinally through said chamber from its base to a position near said closed top, said partition forming said column and said conduit means.

3. The device of claim 1 wherein said variable aperture means comprises a base portion of said container at said second position and a cap member slidingly mounted on said base portion, one of said base portion and said cap member having variable hole means and the other having an aperture of constant size, said cap member and said base portion being in a relationship whereby said constant sized aperture registers with a portion of said variable hole means.

4. The device of claim 3 wherein said variable hole means comprises a plurality of holes varying in size and said constant sized aperture is at least as large as the largest hole of said plurality of holes.

5. The device of claim 4 wherein said plurality of holes are arranged circularly.

6. The device of claim 5 wherein said circularly arranged holes are located in said base portion and said constant sized aperture is located in said cap member, said constant sized aperture being adapted for registering with one of said holes while said cap member closes off the remainder of said holes.

7. The device of claim 5 wherein said circularly arranged holes are located in said cap member and said constant sized aperture is located in said base portion, said constant sized aperture being adapted for registering with one of said holes while the base portion seals the remainder of said holes.

8. The device of claim 3 wherein said variable hole means comprises a slot progressively increasing in width from one end to the other and said constant sized aperture is at least as wide as the widest portion of said slot.

9. The device of claim 8 wherein said slot is substantially circular.

10. The device of claim 9 wherein said slot is located in said base portion and said constant sized aperture is located in said cap member, said constant sized aperture being adapted for registering with a portion of said slot while said cap member closes the remainder of said slot.

11. The device of claim 9 wherein said slot is located in said cap member and said constant sized aperture is located in said base portion, said constant sized aperture being adapted for registering with a portion of said slot while said base portion seals the remainder of said slot.

* * * * *